(12) United States Patent
Lapa et al.

(10) Patent No.: US 7,239,739 B2
(45) Date of Patent: Jul. 3, 2007

(54) APPARATUS FOR GENERATING DATA FOR DETERMINING A PROPERTY OF A GEMSTONE AND METHODS AND COMPUTER PROGRAMS FOR DETERMINING A PROPERTY OF A GEMSTONE

(75) Inventors: Dave Lapa, Antwerpen (BE); Marc Frans Alida Van de Velde, Berlaar (BE); Christiaan Louis Cecile Keersmaekers, Booischot (BE)

(73) Assignee: Overseas Diamonds Technologies, Antwerp (BE)

( * ) Notice: Subject to any disclaimer, the term of this patent is extended or adjusted under 35 U.S.C. 154(b) by 234 days.

(21) Appl. No.: 10/921,441

(22) Filed: Aug. 19, 2004

(65) Prior Publication Data

US 2005/0036132 A1 Feb. 17, 2005

Related U.S. Application Data

(62) Division of application No. 10/107,585, filed on Mar. 25, 2002, now Pat. No. 6,813,007.

(30) Foreign Application Priority Data

Dec. 13, 2001 (EP) .................................. 01310405

(51) Int. Cl.
*G06K 9/00* (2006.01)
(52) U.S. Cl. ..................................................... 382/141
(58) Field of Classification Search ................ 382/141, 382/181, 190, 209
See application file for complete search history.

(56) References Cited

U.S. PATENT DOCUMENTS 3,867,032 A 2/1975 Bruck
3,947,120 A 3/1976 Bar-Issac et al.

(Continued)

FOREIGN PATENT DOCUMENTS

EP 0464824 1/1992

(Continued)

OTHER PUBLICATIONS

Reinitz, et al., Modeling the Appearance of the Round Brilliant Cut Diamond: An Analysis of Fire, and More About Brilliance, Gems & Gemology, Fall 2001, pp. 173-197.

(Continued)

*Primary Examiner*—Vikkram Bali
(74) *Attorney, Agent, or Firm*—Knobbe, Martens, Olson & Bear LLP (57) ABSTRACT

An apparatus for generating data for use in determining a property of a gemstone, such as a cut diamond with a support structure for supporting a gemstone placed at an observation position, the support structure being arranged such that, if the gemstone has an axis of symmetry, the gemstone is supportable such that the axis of symmetry is parallel to an axis X passing through the observation position; an illuminator arranged to illuminate a gemstone so placed with a spatially varied light pattern; a rotator arranged to cause relative rotation between the light pattern and the support structure generally about the axis X; and a camera arranged to capture, at each of a plurality of rotational positions, an image of light returned by the gemstone and to output said images as image data.

8 Claims, 5 Drawing Sheets

U.S. PATENT DOCUMENTS

| | | | |
|---|---|---|---|
| 4,900,147 A | | 2/1990 | Bowley et al. |
| 5,196,966 A | | 3/1993 | Yamashita |
| 5,544,254 A | | 8/1996 | Hartley et al. |
| 5,615,005 A | | 3/1997 | Valente et al. |
| 5,828,405 A | | 10/1998 | Vanier et al. |
| 5,836,205 A | | 11/1998 | Meyer |
| 5,883,388 A | * | 3/1999 | Smith et al. ............. 250/330 |
| 5,966,673 A | | 10/1999 | Shannon, Sr. |
| 6,014,208 A | | 1/2000 | Welbourn et al. |
| 6,020,954 A | * | 2/2000 | Aggarwal ............. 356/30 |
| 6,211,484 B1 | | 4/2001 | Anner et al. |
| 6,239,867 B1 | | 5/2001 | Aggarwal |
| 6,473,164 B1 | | 10/2002 | De Jong et al. |
| 6,813,007 B2 | * | 11/2004 | Lapa et al. ............. 356/30 |
| 2001/0006415 A1 | | 7/2001 | Tolkowsky et al. |

FOREIGN PATENT DOCUMENTS

| | | |
|---|---|---|
| GB | 2332755 | 6/1999 |
| GB | 2358541 A | 7/2001 |
| WO | WO 96/23207 | 8/1996 |
| WO | WO 99/61890 | 12/1999 |
| WO | WO 01/36214 | 5/2001 |

OTHER PUBLICATIONS

GemEx Systems, Inc., Brilliance Scope™ Analyzer Demonstration, at http://www.gemex.com/bScopeapplet/index.html.

GemEx Systems, Inc., What People are Saying About the Brilliance Scope™ Technology, http://www.gemex.com/consumer/quotes.html (Oct. 26, 2001).

GemEx Systems, Inc. Gemspec Imaging Spectrophotometer, at http://www.gemex.com (1996).

GemEx Systems, Inc. Brilliance Scope™ Viewer, Light Performance A Consumer Can see, at http://www.gemex.com.

GemEx Systems, Inc. The Guide Light Performance Analysis, at http://www.gemex.com (2002).

GemEx Systems, Inc. website, http://www.gemex.com/htmdocs/consumer/the_whole_story.html 4 pgs, Copyright 2002 GemEx Systems, Inc.

* cited by examiner

APPARATUS FOR GENERATING DATA FOR DETERMINING A PROPERTY OF A GEMSTONE AND METHODS AND COMPUTER PROGRAMS FOR DETERMINING A PROPERTY OF A GEMSTONE

CROSS REFERENCE TO RELATED APPLICATION

This application is a divisional of U.S. patent application Ser. No. 10/107,585 entitled "APPARATUS FOR GENERATING DATA FOR DETERMINING A PROPERTY OF A GEMSTONE AND METHODS AND COMPUTER PROGRAMS FOR DETERMINING A PROPERTY OF A GEMSTONE" filed on Mar. 25, 2002 now U.S. Pat. No. 6,813,007. The disclosure of the above-described filed application is hereby incorporated by reference.

FIELD OF INVENTION

The present invention relates to electronic apparatus for generating data for determining properties of gemstones, such as cut diamonds, as well as methods of and computer programs for determining properties of gemstones using the generated data. In particular, but not exclusively, it relates to electronic apparatus for generating data for determining properties as well as methods of and computer programs for determining properties of gemstones in which a plurality of images of the gemstone are captured for analysis under different lighting conditions.

BACKGROUND OF THE INVENTION

The beauty of a gemstone, such as a cut diamond, derives from its light handling ability. What attracts the eye is the "game of light" played by a well-cut diamond as incident light is reflected and refracted off its many facets. Diamonds and other gemstones may be cut according to many different standardised cut patterns such as the standard round brilliant cut, oval, pear, marquise, radiant, princess, heart, emerald cut etc. The most popular cut is the standard round brilliant (SRB) cut as shown in FIG. 1. Diamond cutting and polishing is a highly skilled art and a well-cut diamond, having superior optical performance, will command a significant price premium over a poorly cut diamond having inferior optical performance.

When showing a cut diamond to an untrained observer, one frequently refers to the four C's of a gemstone, being its carat weight, its clarity, its cut and its colour. Carat weight, clarity and colour can be relatively easily measured objectively and are therefore generally useful. Cut may also be specified or measured in terms of the geometry of the various facets. However, what really matters is the light handling ability of the gemstone and reference is often made to more subjective parameters of a cut diamond, such as its brilliance (the intensity of light returned), scintillation (fast and local fluctuations in the light returned as the diamond moves relative to the lighting conditions), fire (the dispersion of white light into spectral colours) and symmetry (the symmetry of light patterns such as the so-called "hearts and arrows"). It can be difficult, particularly for an untrained observer, to make a personal appraisal of these subjective parameters. It can also be difficult to compare the light handling abilities of two diamonds with the same carat weight, clarity and colour, and therefore to appreciate why one is more valuable than the other.

It is recognised that properties such as brilliance, fire and symmetry should be derived, whether by experimental observation or theoretical computer modelling, under a variety of lighting conditions. Moreover, with the property of scintillation it is clearly essential to observe or model the diamond under a variety of lighting conditions. Electronic apparatus for capturing images of gemstones under varying lighting conditions for analysis are known.

DESCRIPTION OF THE RELATED TECHNOLOGY

International Patent Publication number WO 96/23207 describes a device which captures colour images of a gemstone placed in an analysis chamber and illuminated by a uniform annular light which may be moved along an axis such that the gemstone may be illuminated from a plurality of different angles. The device performs a spectral analysis of the captured images using a tuneable optical band pass filter to determine the colour of the gemstone. Digital images of the gemstone may also be stored, displayed or transmitted over a data network.

The website (www.gemex.com) of GemEx Systems, Inc, a US company, describes a device called the BrillianceScope Analyser which is described as an imaging spectrophotometer. Colour images of a diamond are captured in a controlled lighting environment consisting of six lighting angles, five of which provide reflected light and one of which provides diffuse lighting. These images may then be analysed to generate a report on the diamond. The BrillianceScope Analyser device operates on the same principle as the device described in International Patent Publication number WO 96/23207 referred to above, in that the gemstone is placed in an analysis chamber and illuminated by a uniform annular light which may be moved along an axis such that the gemstone is illuminated from different angles. The images may be analysed by a computer, and the properties of "white light", "coloured light" and "scintillation" for a diamond are determined and displayed on three line chart scales from 'low', to 'medium' to 'high'. Captured images may also be shown in a repeating sequence in one display area, giving the effect of light movement.

International Patent Publication number WO 99/61890 describes a system for the standardised grading of gemstones. A gemstone is subject to a plurality of incident light sources and images are captured for analysis. Images of the gemstone, such as a SRB cut diamond, may be captured from various viewpoints such as from the pavilion, from the crown and side-on. The gemstone is supported by a rotatable platform which is rotated when images are being captured from a side-on viewpoint to obtain profile and colour images from a variety of rotational positions and to detect internal flaws and inclusions. When capturing images from above and below the gemstone, the platform is moved along an axis from a level position to a down and an up position respectively. The fixed focal length camera is also moved along an axis to focus on the gemstone when the platform is moved between the up, down and level positions. A captured image may be analysed by a processor to obtain colour measurements and measures of the brilliance and scintillation of the gemstone.

One object of the present invention is to provide an electronic apparatus, method and computer program for generating data for improved determination of properties of a gemstone, such as brilliance, scintillation, fire and symmetry.

Another object of the present invention is to provide an electronic apparatus for generating data for determining properties of gemstones which is more compact, lightweight, mechanically simpler, and therefore less expensive to manufacture, than conventional apparatus, making it more suitable for use in retail premises, such as jewellers shops.

Another object of the present invention is to provide an electronic apparatus, method and computer program enabling a observer to more easily compare two diamonds and their properties, in particular the properties of brilliance, scintillation, fire and symmetry.

Another object of the present invention is to provide an electronic apparatus, method and computer program for generating data for determining properties of a cut gemstone which is adapted to and takes into account attributes of the shape and/or symmetry of the cut pattern of a particular gemstone.

Another object of the present invention is to provide an electronic apparatus, method and computer program for generating data for determining properties of a gemstone in which the gemstone is illuminated under more realistic lighting conditions.

Another object of the present invention is to provide an electronic apparatus, method and computer program for measuring the symmetry of a gemstone in terms of the light returned.

SUMMARY OF CERTAIN INVENTION ASPECTS

According to a first aspect of the present invention there is provided an apparatus for generating data for use in determining a property of a gemstone, such as a cut diamond, the apparatus comprising:

a support structure for supporting a gemstone placed at an observation position, the support structure being arranged such that, if the gemstone has an axis of symmetry, the gemstone is supportable such that the axis of symmetry is parallel to an axis X passing through the observation position;

an illuminator arranged to illuminate a gemstone so placed with a spatially varied light pattern;

a rotator arranged to cause relative rotation between the light pattern and the support structure generally about the axis X; and a camera arranged to capture, at each of a plurality of rotational positions, an image of light returned by the gemstone and to output said images as image data.

By rotating the spatially varied light pattern relative to the supported gemstone about the axis of symmetry of the gemstone, and capturing images at a plurality of rotational positions, the apparatus is particularly adapted to determining properties of cut gemstones having radially symmetric cut patterns, such as SRB cut diamonds. The intensity levels, and colour component proportions, of light returned at any particular spatial region of the gemstone are sensitive to rotational movement. Thus, brilliance, symmetry, fire and scintillation are more easily, accurately and objectively measurable. Furthermore, unlike the prior art referred to above, which are generally mechanically complex, and have laterally moving parts for varying the lighting conditions, the apparatus of the present invention advantageously employs rotationally moving parts for varying the lighting conditions, thus enabling the apparatus to be manufactured in a relatively compact and lightweight form, and relatively inexpensively.

In preferred embodiments, the light pattern comprises at least one relatively light region and at least one relatively dark region, the regions being arranged radially about the axis X. Preferably, the light pattern is generally symmetrical about the axis X. Also preferably, the light pattern has an n-fold symmetry, such as a 4-fold or 8-fold symmetry, where n is a whole number multiple or factor of s, a standardised gemstone cut having an s-fold symmetry.

Thus, the light pattern illuminating the gemstone, corresponds closely to particular gemstone cut patterns, such as the SRB cut, which have a particular shape and a particular arrangement of radially symmetric facets, resulting in the images captured having greater contrast levels between different spatial regions of the gemstone and the intensity levels, and colour component proportions, of light returned at any particular spatial region of the gemstone having greater sensitivity to rotational movement. Thus, brilliance, symmetry, fire and scintillation are more easily, accurately and objectively measurable. Furthermore, the light pattern illuminating the gemstone is a more realistic simulation of the light that would illuminate a gemstone in normal, everyday use—for instance when mounted in an item of jewellery such as a ring. Light is not normally uniform around the axis of symmetry of the diamond and incident only at a narrow range of angles off the axis, as in prior art approaches. Instead, light is normally incident at a wide range of angles off the axis of symmetry of the diamond and not uniform around the axis as in the present invention.

In other preferred embodiments, the illuminator comprises a reflector having a concave surface arranged to reflect light generally towards the gemstone, the concave surface having at least one relatively reflective region and at least one relatively unreflective region, thereby creating said light pattern. Preferably, the reflector is rotatably mounted in said apparatus generally about the axis X, thereby enabling relative rotation between the light pattern and the support structure generally about the axis X. Alternatively, the platform is rotatably mounted in said apparatus generally about the axis X, thereby enabling relative rotation between the light pattern and the support structure generally about the axis X. Preferably, the illuminator comprises an annular light source arranged to emit light towards the concave surface and an annular baffle arranged to prevent direct light reaching the gemstone.

Thus, the apparatus requires only a single stationary light source and a rotatable reflector or rotatable support structure to enable rotation of the light pattern relative to the supported gemstone, resulting in improved mechanical simplicity, as well as reduced size, weight and cost of manufacture.

In a further preferred embodiment, the apparatus comprises a data processing device arranged to determine a property of the gemstone by comparing, using image data corresponding to one or more of said electronic images, the intensity of light at a first and a second image portion, each portion comprising one or more pixels, said first and second image portions corresponding to a first and a second region of the gemstone respectively, said first and second regions being related to each other in accordance with a symmetrical property of a standardised gemstone cut.

Thus, an objective measurement of the symmetry of a gemstone is enabled in terms of the actual light returned from the gemstone and the expected symmetry of the gemstone, such as the 8-fold symmetry of an SRB cut diamond, rather than based on potentially unrealistic or inaccurate models of the geometry of the cut pattern of the gemstone.

In a further preferred embodiment, the apparatus comprises a data processing device arranged to determine a property of the gemstone by comparing, using image data corresponding to two of said electronic images, the intensity of light at one or more pixels of a first image, captured at a first rotational position, with the intensity of light at one or more pixels of a second image, captured at a second rotational position different to said first rotational position, said one or more pixels of the first image corresponding to the same region or regions of the gemstone as said one or more pixels of the second image.

Thus, an improved objective measurement of scintillation is enabled, using data from a plurality of images obtained at different rotational positions of the spatially varied light pattern. With cut gemstones having cut patterns with many radial facets, such as the SRB cut with 32 differently angled facets in the crown and 24 differently angled facets in the pavilion, scintillation may be measured more accurately as, in particular, the intensity levels of returned light have a greater sensitivity to rotational movement of the light pattern relative to the gemstone than to variation of the angle of incidence of the light source.

In a further preferred embodiment, the apparatus comprises a data processing device arranged to determine a property of the gemstone by comparing, using image data corresponding to two of said electronic images, the proportions of colour components at one or more pixels of a first image, captured at a first rotational position, with the proportions of colour components at one or more pixels of a second image, captured at a second rotational position different to said first rotational position, said one or more pixels of the first image corresponding to the same region or regions of the gemstone as said one or more pixels of the second image.

Thus, an improved objective measurement of fire is enabled, using data from a plurality of images obtained at different rotational positions of the spatially varied light pattern. With cut gemstones having cut patterns with many radial facets, such as the SRB cut with 32 differently angled facets in the crown and 24 differently angled facets in the pavilion, fire may be measured more accurately as, in particular, the proportions of colour components of returned light have a greater sensitivity to rotational movement of the light pattern relative to the gemstone than to variation of the angle of incidence of the light source.

According to a second aspect of the present invention there is provided a method of generating data for use in determining a property of a gemstone, such as a cut diamond, the method comprising:
  supporting a gemstone at an observation position, such that, if the gemstone has an axis of symmetry, the gemstone is supportable such that the axis of symmetry is parallel to an axis X passing through the observation position;
  illuminating the gemstone with a spatially varied light pattern;
  causing relative rotation between the light pattern and the gemstone generally about the axis X;
  capturing, at each of a plurality of rotational positions, an image of light returned by the gemstone.

According to a third aspect of the present invention, there is provided a method of determining a property of a gemstone by comparing, using image data corresponding to one or more electronic images of the gemstone, the intensity of light at a first and a second image portion, each portion comprising one or more pixels, said first and second image portions corresponding to a first and a second region of the gemstone respectively, said first and second regions being related to each other in accordance with a symmetrical property of a standardised gemstone cut.

According to a fourth aspect of the present invention, there is provided a method of determining a property of a gemstone by comparing, using image data corresponding to two or more electronic images of the gemstone captured under different lighting conditions, the intensity of light at one or more pixels of a first image, captured under a first lighting condition, with the intensity of light at one or more pixels of a second image, captured under second different lighting condition, said one or more pixels of the first image corresponding to the same region or regions of the gemstone as said one or more pixels of the second image.

According to a fifth aspect of the present invention, there is provided a method of determining a property of the gemstone by comparing, using image data corresponding to two or more electronic images of the gemstone captured under different lighting conditions, the proportions of colour components at one or more pixels of a first image, captured under a first lighting condition, with the proportions of colour components at one or more pixels of a second image, captured under a second different lighting condition, said one or more pixels of the first image corresponding to the same region or regions of the gemstone as said one or more pixels of the second image.

According to a sixth aspect of the present invention, there is provided a computer-implemented method of comparing properties of gemstones, such as cut diamonds, the method comprising:
  receiving first image data in respect of a first gemstone and second image data in respect of a second gemstone, said first and second image data each comprising one or more images of said first and second gemstones, respectively;
  determining a property of each of said first and second gemstones in dependence on said first and second image data respectively; and
  simultaneously displaying one or more images of each of said first and second gemstones together with a representation of the determined property for each of said first and second gemstones.

Thus, an observer, such as a potential purchaser untrained in evaluating properties of gemstones, may compare two gemstones by means of a side by side graphical representation on a computer screen and by means of objectively determined properties, such as brilliance, scintillation, fire and symmetry.

According to a seventh aspect of the present invention, there is provided a apparatus for comparing properties of gemstones, such as cut diamonds, the apparatus comprising:
  a support structure for supporting a gemstone placed at an observation position;
  an illuminator arranged to illuminate a gemstone so placed;
  a camera arranged to capture an image of light returned by a gemstone and to output said images as image data; and
  a data processing device arranged to:
    receive first image data in respect of a first gemstone and second image data in respect of a second gemstone, said first and second image data each comprising one or more images of said first and second gemstones, respectively;
    determine a property of each of said first and second gemstones in dependence on said first and second image data respectively; and simultaneously display one or more images of each of said first and second gemstones together with a representation of the determined property for each of said first and second gemstones.

Due to the compact, lightweight and inexpensive format of the apparatus, the gemstone analysis and comparison may be performed in retail premises, such as in a jeweller shop, with the potential purchaser present.

According to a eighth aspect of the present invention, there is provided an apparatus for generating data for use in determining a property of a gemstone, such as a cut diamond, the apparatus comprising:

a support structure for supporting a gemstone placed at an observation position, the support structure being arranged such that, if the gemstone has an axis of symmetry, the gemstone is supportable such that the axis of symmetry is parallel to an axis X passing through the observation position;

an illuminator arranged to illuminate a gemstone so placed with a spatially varied light pattern;

a rotator arranged to cause relative rotation between the light pattern and the support structure;

a camera arranged to capture, at each of a plurality of rotational positions, an image of light returned by the gemstone generally along the axis X and to output said images as image data.

According to a ninth aspect of the present invention, there is provided a apparatus for generating data for use in determining a property of a gemstone, such as a cut diamond, the apparatus comprising:

a support structure for supporting a gemstone placed at an observation position;

an illuminator arranged to illuminate a gemstone so placed with a spatially varied light pattern;

a rotator arranged to cause relative rotation between the light pattern and the support structure generally about an axis X passing through the observation position;

a camera arranged to capture, at each of a plurality of rotational positions, an electronic image of light returned by the gemstone generally along the axis X and to output said images as image data.

According to a tenth aspect of the present invention, there is provided a apparatus for generating data for use in determining a property of a gemstone, such as a cut diamond, the apparatus comprising:

a support structure for supporting a gemstone placed at an observation position;

an illuminator arranged to illuminate a gemstone so placed with a spatially varied light pattern;

a rotator arranged to cause relative rotation between the light pattern and the support structure generally about an axis X passing through the observation position;

a camera arranged to capture, at each of a plurality of rotational positions, an electronic image of light returned by the gemstone and to output said images as image data.

Further aspects and features of the present invention are set out in the appended claims, and further advantages will be apparent from the following description, given by way of example only, in which:

DETAILED DESCRIPTION OF CERTAIN INVENTIVE EMBODIMENTS

Figure 1A:
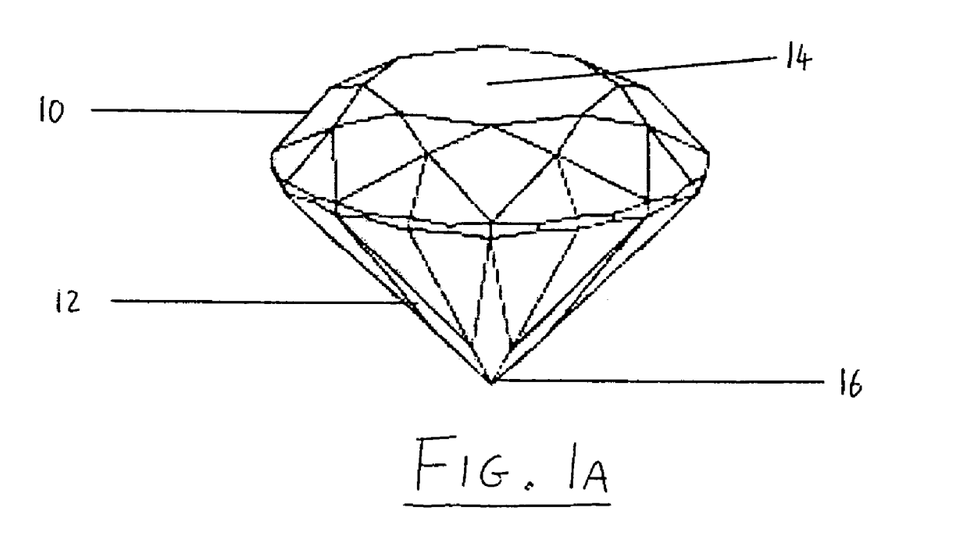
FIGS. 1a and 1b show a standard round brilliant cut diamond from an elevated side-on perspective and from a top-down view, respectively.
Figure 1B:
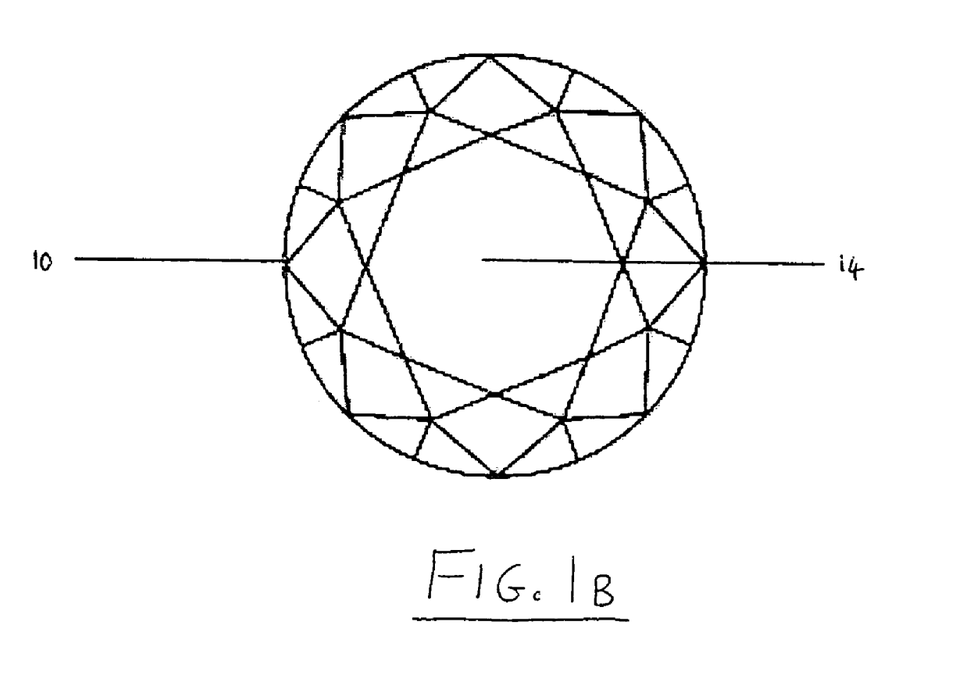

FIGS. 1a and 1b show the geometry of a standard round brilliant (SRB) diamond. FIG. 1a shows the diamond from an elevated side-on view. The top most domed-shaped portion of the diamond is known as the crown 10. The bottom most conical portion of the diamond is known as the pavilion 12. At the top of crown 10 at the centre is a relatively large facet known as the table 14. The bottom most point of the pavilion 12 is known as the culet 16. FIG. 1b shows the SRB diamond from a top-down view, looking along an axis from the centre of the table 14 through the culet 16. There are 32 facets on the crown 10 of the SRB cut diamond, not including table 14, and 24 facets on the pavilion, not including culet 16. It can be seen that the radial facets of the SRB cut diamond (56 in total plus one for the table and one for the culet) have an 8-fold symmetry about an axis passing though the centre of table 14 and culet 16.

Figure 2:
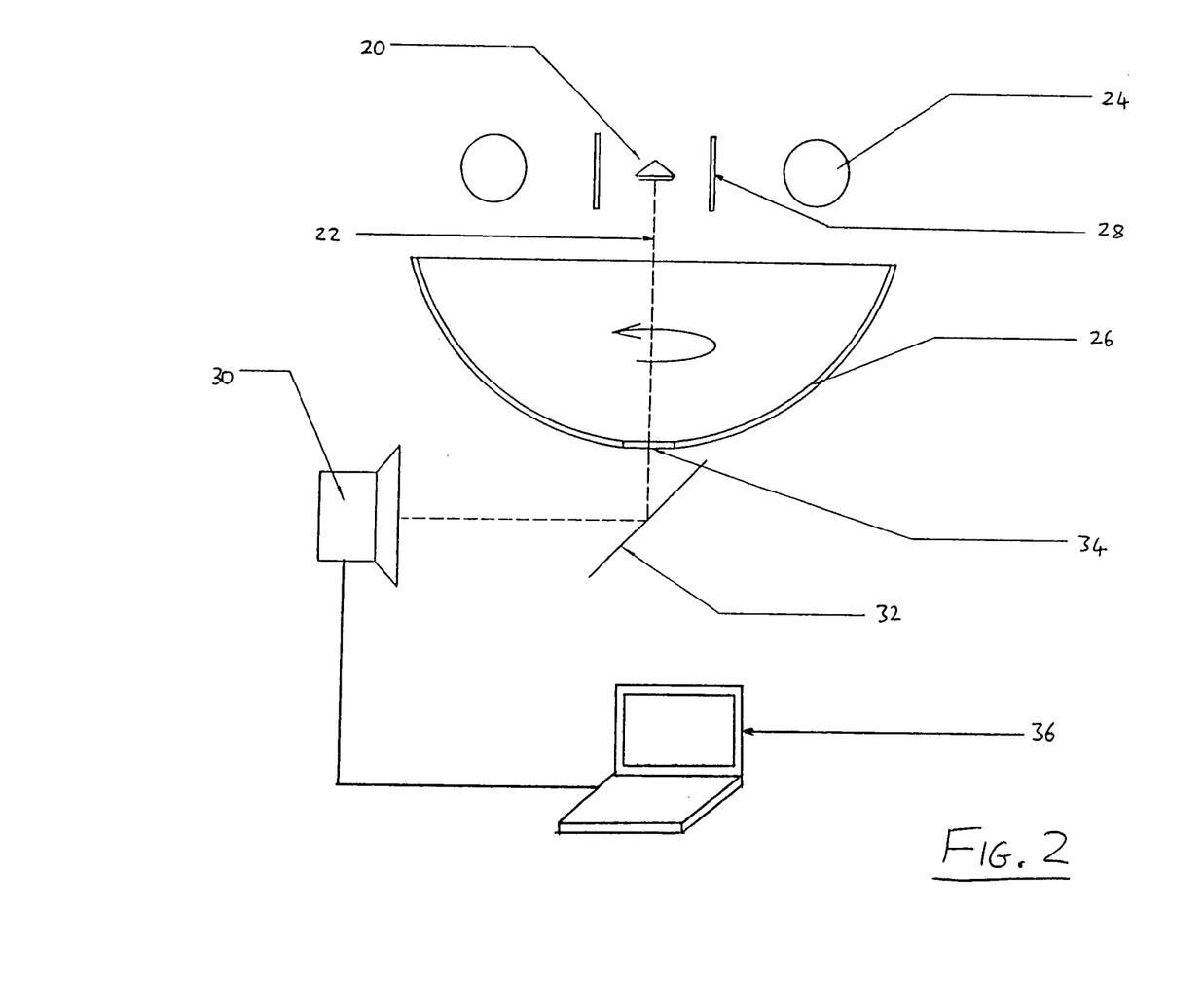
FIG. 2 shows an apparatus for generating data for determining a property of a gemstone according to the present invention.

FIG. 2 shows a cross-sectional view of an apparatus for generating data for determining properties of a gemstone according to the present invention. A gemstone such as a cut diamond 20 is placed on a platform (not shown) at an observation position with its table-side face-down. The platform is an optically clear glass plane of regular thickness arranged within the apparatus so that it is substantially horizontal when the apparatus is in a horizontal position. The platform may be coated with an anti-reflection coating and provided with a small ring underneath to reduce glare. The apparatus is mounted in a housing (not shown) which prevents external light from reaching the diamond 20 and dust from entering the mechanical and optical components. The housing has a access lid above the platform for placing and removing a gemstone to be measured. The inner surface of the housing and lid above the region of the platform is coated with an unreflective material so that substantially no light is reflected back from the lid or housing towards the gemstone or platform.

Diamond 20 is illuminated by an annular light 24, such as a fluorescent tube light or halogen light. Annular light 24 emits visible light of frequency comparable to daylight. A suitable annular light is a Stocker and Yale microscope illuminator with a White 5500 HC fluorescent ring light having a colour temperature of 5500° K, which produces a light close to Northern daylight. Light from annular light 24 is prevented from directly reaching diamond 20 by an annular baffle 28 disposed between the annular light 24 and the diamond 20. However, light from annular light 24 is reflected off a concave surface 26 of a reflector and generally towards diamond 20. The reflector may be a semi-spherical shell centred on the observation position with the inner surface of the shell being concave surface 26.

The reflector is mounted within the apparatus such that concave surface 26 is rotatable about an axis 22 perpendicular to the platform and such that when diamond 20 is placed at the observation position, the centre of its table and its culet lie approximately along axis 22. Annular light 24 and annular baffle 28 are stationary and disposed within the apparatus such that they are also perpendicular to and centred around axis 22. A stepper motor (not shown) is provided for rotating the reflector, and concave surface 26, about axis 22.

A viewing hole 34 is present at the bottom of the reflector and concave surface 26 where they meet axis 22. A digital camera having a charged couple device (CCD) sensor array, or a complementary metal-oxide semiconductor (CMOS) sensor array, and capable of being controlled by a personal computer (PC), is positioned within the apparatus such that it can capture an image of diamond 20 along the axis 22. The camera is a colour camera having a fixed focal length, at least a 640×480 resolution, a memory capable of storing at least one image, and a data communication interface, compatible with standards such as the Universal Serial Bus (USB), RS 422 parallel port or IEEE 1394 "Firewire" standards, for transferring captured image data to an external device, such as a PC. The camera is focussed on the plane made by the topmost surface of the platform on which diamond 20 is placed, and has a suitable depth of field such that sharp images may be captured of gemstones of the largest size reasonably expected to be measured. An optically clear mirror 32 may be disposed within the apparatus so that the light path between camera 30 and diamond 20 need not be a straight line, thereby enabling a more compact format of apparatus. A suitable digital CCD camera is a Unibrain Fire-i Digital CCD colour camera with a resolution of 640×480 or a Unibrain Fire-i400 Industrial version with a similar resolution. A suitable digital CMOS camera is a Silicon Imaging MegaCamera SI-3170 RGB camera, with a maximum resolution of 2056×1560, a 12-bit per pixel colour depth.

The apparatus, including the light 24, baffle 28, reflector with concave surface 26, mirror 34, stepper motor, camera 30, and housing, but not including the PC, is compact in size (having dimensions of approximately 123 mm×112 mm×200 mm ) and lightweight (approximately 3.875 kg).

Camera 30 and the stepper motor are connected to and controllable by a PC 36. PC 36 may be a portable PC such as a laptop or notebook computer having an Intel Pentium III central processing unit (CPU), 128 megabytes of memory, an LCD panel screen and a 10 gigabyte hard disc drive. PC 36 has a USB port, a parallel port and/or IEEE 1394 "Firewire" port for connecting to the camera and stepper motor, and a 2D video processing chipset for frame grabbing. By means of a suitable computer program, as will be described in greater detail below, PC 36 controls the stepper motor to rotate concave surface 26 through a series of predetermined rotational positions. PC 36 also controls camera 30 to capture images of diamond 20 at a suitable frame rate such that an image may me stored at each of the series of rotational positions of concave surface 26. The image data captured by camera 30 is transferred to PC 36 in the form of a bitmap or other suitable image file format for display and analysis. The image data is transmitted as a continual live image feed to the PC 36.

The range of angles through which concave surface 26 is rotated is dependent upon the symmetry of the light pattern reflecting off concave surface 26. With a light pattern having a 4-fold symmetry, for example, images are captured at a plurality of rotational positions as concave surface 26 is rotated through a 90° range. Within the range, the number of images captured at different rotational positions for use in analysis depends on the cut pattern of the gemstone being measured, or the cut pattern of the most faceted gemstone likely to be measured. Generally, the number of images should be at least 4 times the number of differently angled facets within the range through which concave surface 26 is rotated. Thus, with a SRB cut diamond having 32 differently angled facets in its crown and pavilion and thus 8 differently angled facets within a 90° range, at least 32 images (4*8) should be captured over the 90° range. For general purpose, it has been found that a generally suitable number of images to be captured is 45. Thus, over a 90° range, concave surface 26 is rotated in steps of 2°. It will be understood that higher or lower numbers of images may be used as appropriate to the cut pattern of the gemstone, the accuracy of measurement required and the processing capabilities of the PC 36.

Figure 3A:
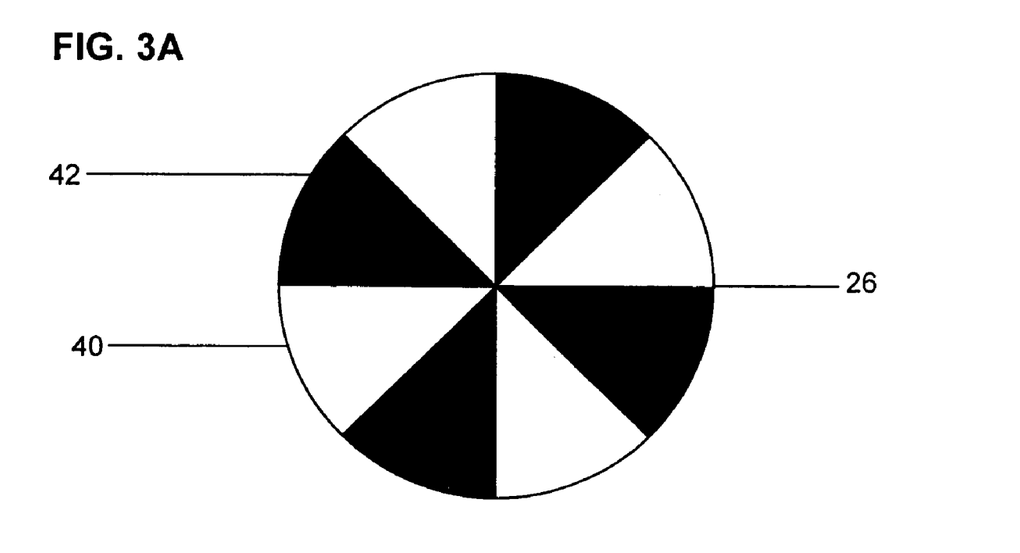
FIGS. 3a and 3b show the concave surface 26 of the apparatus of FIG. 2 having exemplary patterns of relatively reflective and relatively unreflective regions.
Figure 3B:
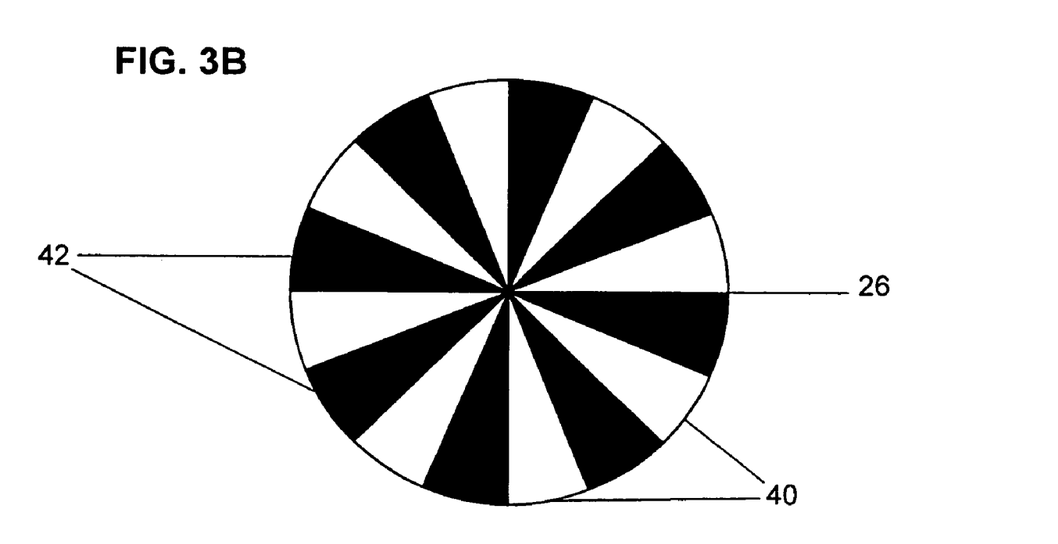

FIGS. 3*a* and 3*b* show the concave surface 26 looking down from the diamond observation position along axis 22. Concave surface 26 has a plurality of relatively reflective regions 40 and relatively unreflective regions 42 formed by coating the surface with relatively reflective and relatively unreflective materials . FIG. 3*a* shows one configuration of regions 40 and 42 in which concave surface 26 is divided into eight equal radial sectors, arranged around the axis 22, which are alternately relatively reflective and relatively unreflective. FIG. 3*b* shows a further configuration of regions 40, 42 in which concave surface 26 is divided into 16 equal sectors, arranged around the axis 22, of alternate relatively reflective and relatively unreflective regions. It can be seen that the configuration of regions 40 and 42 of FIG. 3*a* each have a four-fold symmetry about the axis 22 whereas the configuration of regions 40 and 42 of FIG. 3*b* each have an eight-fold symmetry about axis 22. Other configurations of relatively reflective regions 40 and relatively unreflective regions 42 are envisaged within the scope of the present invention. Concave surface 26 may have a matt finish.

During operation of the apparatus, it can be seen that the light reflecting off concave surface 26 towards the diamond 20 at its observation position has a spatially varied pattern determined by the configuration of relatively reflective regions 40 and relatively unreflective regions 42. In particular, the light pattern, as observed in the plane of the platform, will have a series of radial peaks and troughs of light intensity corresponding to the configuration. Thus, with the configuration of FIG. 3*a*, the light pattern will have four radial peak lines and four radial trough lines. Similarly, with the configuration of FIG. 3*b*, the light pattern will have 8 radial peaks and 8 radial troughs. Furthermore, with diamond 20 table-side down on the platform, the light will be reflected generally towards the crown at a broad range of angles of incidence relative to axis 22, as predominantly occurs when diamonds are mounted in rings and other jewellery for everyday use.

The selection of a particular configuration of relatively reflective regions 40 and relatively unreflective regions 42 is dependent upon the standardised cut of diamond 20. For example, a diamond of SRB cut has an eight-fold symmetry as described above, and a suitable configuration of regions 40 and 42 would be that as shown in FIG. 3*a*, in which there are eight sectors in total—four relatively reflective sectors 40 and four relatively unreflective sectors 42. Thus, the light pattern reflecting of concave surface 26, having four radial peaks and four radial troughs corresponds to the symmetry of the cut gemstone in that adjacent symmetrical sectors of the gemstone (of 45°) will receive corresponding radial light pattern sectors (of 45°) having adjacent peaks and troughs. As concave surface 26 is rotated through 90°, the intensity of light as observed at any radial line in the plane of the platform and about axis X, will go through a single complete cycle having a single peak and a single trough.

PC 36 may run a standard operating system, such as Microsoft Windows XP or the like. PC 36 also executes a computer program arranged to control the stepper motor to rotate concave surface 26 and to control camera 30 to capture and transfer to PC 36 images of diamond 20 at each of the predetermined rotational positions, for example, 45 images taken at rotational steps of 2° over a total range of 90°. Control over the stepper motor is achieved by using a conventional stepper motor control circuit, such as a Motorola MC 3479 stepper motor controller, to interface between PC 36 and the stepper motor and executing corresponding program elements on PC 36 for sending digital control signals to the stepper motor control circuit. Control over camera 30 is achieved using the camera's inbuilt control interface and executing corresponding program elements on PC 36 for sending digital control signals to camera 30.

Figure 4:
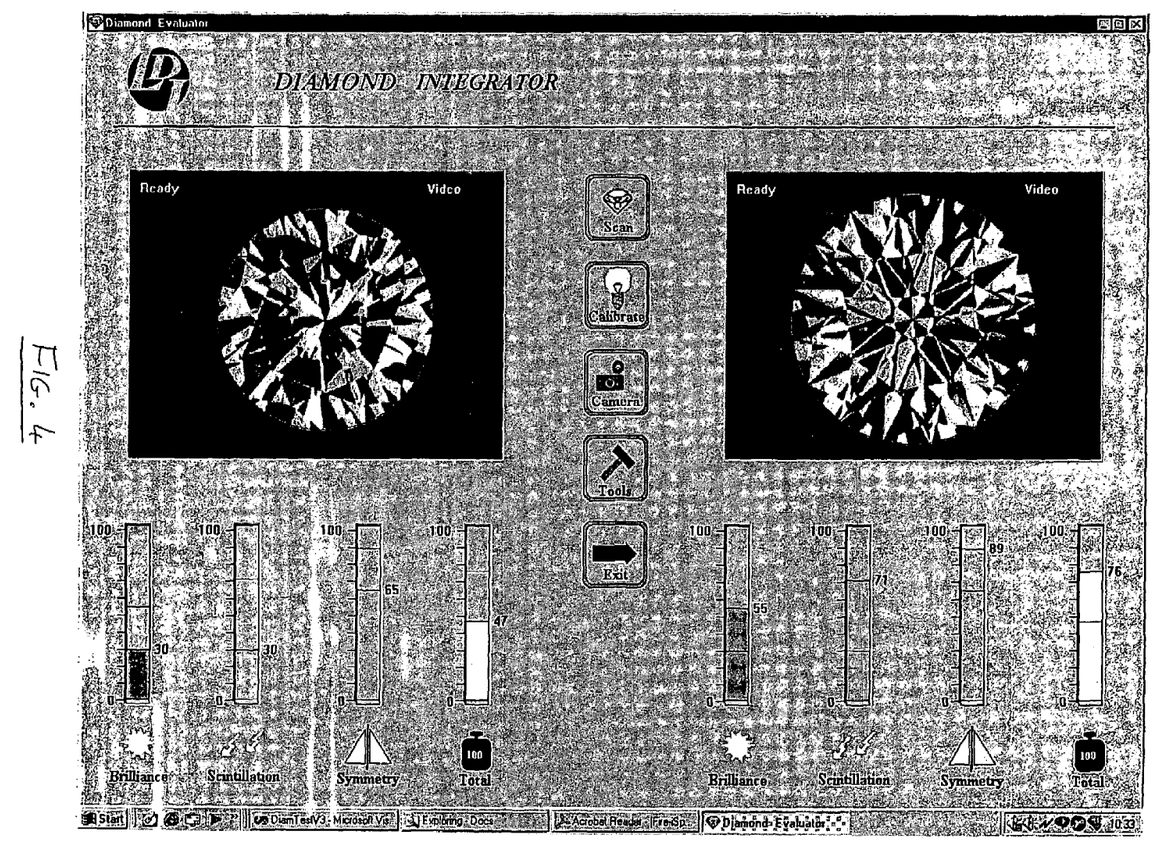
FIG. 4 shows a screen shot of the main screen of a computer program for analysing images of gemstones according to the present invention.

The program elements controlling the stepper motor and camera 30 are themselves under control of a main computer program executing on PC 36 and able to receive user instructions via a user interface to cause the series of images of diamond 20 to be captured and transferred from camera 30 to the PC 36, to analyse the images using various algorithms to obtain measurements of optical properties of diamond 20 and to display the images on the screen of the PC 36. FIG. 4 shows a screen shot of the main menu screen of the computer program. On the right and left sides of the main menu screen are images of two different diamonds, captured in separate scanning operations. An image of a diamond on the right or left sides of the main menu screen may be a "live" image as currently being captured by camera 30 or a "video" image as previously captured during a scanning operation and stored in the hard disk drive of the PC 36. A "video" image may be presented as a moving image with the diamond being shown in consecutive rotational positions. Beneath each image are measurements of the diamond's optical properties of brilliance, scintillation and symmetry represented in numerical format (0 to 100) and as a graphical bar chart. Algorithms for calculating these measurements will be described below. An average of the three measurements is also provided labelled "Total" giving an overall measure of the three optical properties. Thus, a user, such as prospective buyer can compare two diamonds, scanned in two separate scanning operations, side by side both visually on PC 36 screen and in terms of objective measurements of the optical properties of brilliance, scintillation and symmetry.

Five push buttons are presented in the centre of the screen for user control of the computer program and apparatus. A "Scan" push button is provided for causing the computer program to initialise a scan of diamond 20. Initially, diamond 20 is manually placed table-side down on the platform and centred on axis 22. This may be assisted by observing the live image of the diamond displayed on PC 36 screen. Then, the stepper motor is controlled to rotate concave surface 26 to a "home" position and then to each of the series of rotational positions, for example 45 positions over a 90° range in steps of 2°. Frames grabbed from camera 30 at each of these positions are stored in the hard disc drive of PC 36 for later display and analysis. The results of analysis, ie the measurements of brilliance, scintillation and symmetry, are then displayed.

A "Calibrate" push button is provided for calibrating the system to compensate for variations in the intensity of the light produced by annular light 24. Calibration is performed by rotating concave surface 26 to a predetermined position, and placing an angled mirror on the platform in a predetermined position, such that camera 30 views a known portion of concave surface 26. The known portion concave surface 26 may comprise relatively reflective and relatively unreflective regions 40, 42. An image captured by camera 30 of the known portion of concave surface 26 is then analysed by integrating the light intensity levels over all pixels to determine a total light intensity level received. The total light intensity level is then used to adjusts gain and brightness settings of camera 30. Calibration is preferably performed at regular intervals and immediately prior to scanning.

A "Camera" push button is provided for altering the default settings of the camera. A "Tools" push button is provided for selecting various options for the computer program such as a) whether the computer program determines the circumference of a gemstone automatically or manually; b) if manually, for providing a user interface to indicate it; c) how fast concave surface 26 is rotated; and d) the frequency with which stored frames, captured at different rotational positions, are sequentially displayed on the screen of PC 36. An "Exit" push button is also provided for closing exiting the computer program.

To calculate the three measures of brilliance, scintillation and symmetry, from the stored images, three separate algorithms are used. In each case, the main computer program first analyses the images to determine the circumference of diamond 20 and its centre point. The circumference is determined by first summing the light intensity levels at each pixel over all the images at different rotational positions, for example 45 images, to obtain a composite image. Then, all pixels of the composite image having a light intensity level above a predetermined threshold (representing a light level slightly above the level of the black background) are selected. Then the smallest circle containing all the selected pixels is determined and this is defined as the circumference of diamond 20.

Figure 5:
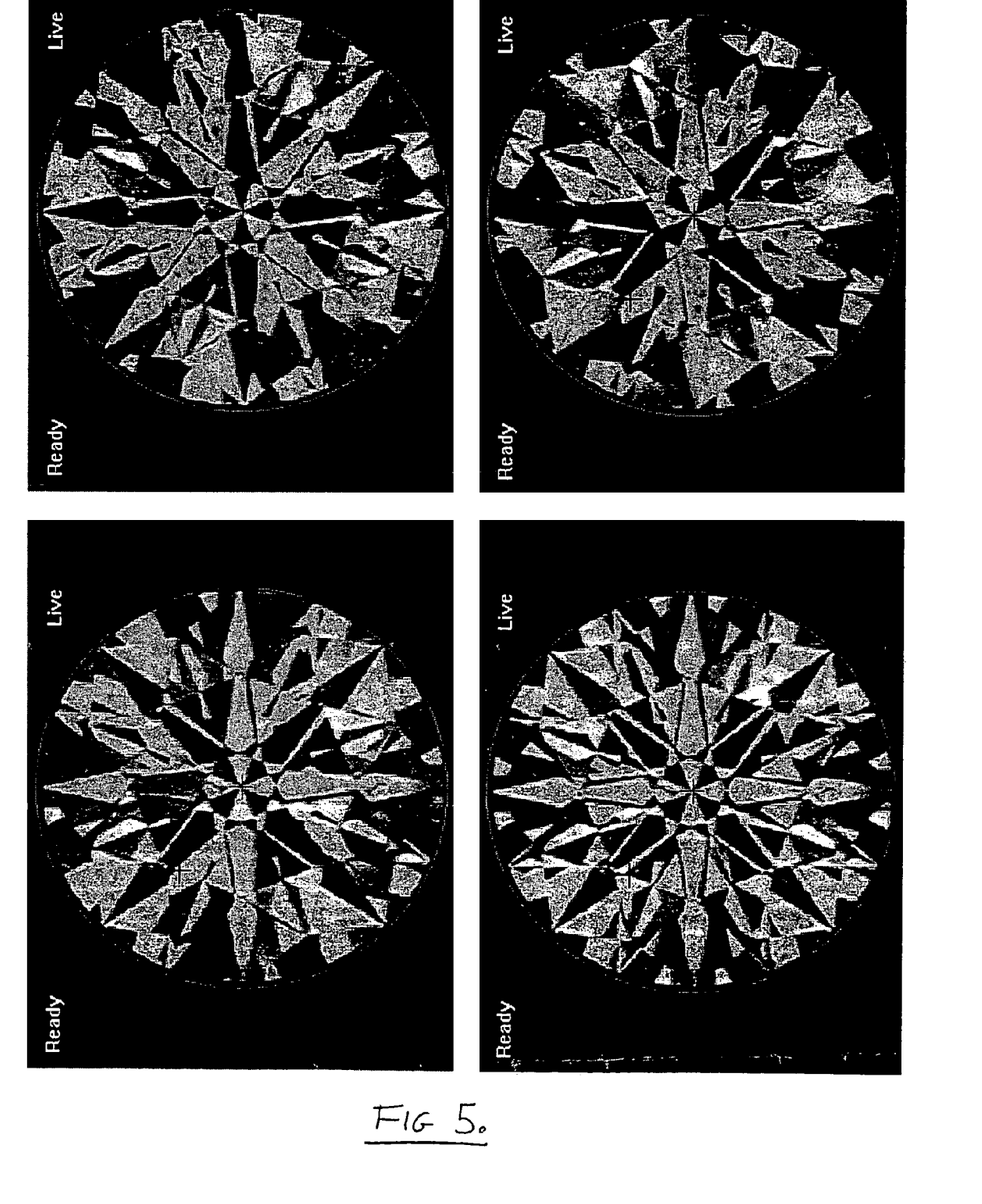
FIG. 5 shows four images of a cut diamond captured a different rotational positions.

Once the circumference and centre of diamond 20 is determined, the three algorithms are executed to calculate measurements of the three optical properties only in respect of pixels contained within the circumference and excluding pixels outside the circumference. FIG. 5 shows four images of a cut diamond captured at different rotational positions together with a circle defining the circumference of the diamond and a cross marking the centre point. It can be seen that various geometrical patterns of light and dark regions are formed and, in different rotational positions, the regions appear either relatively light or relatively dark.

To calculate a measure of the brilliance of diamond 20, the average light intensity level (ie brightness) is determined over each pixel within the circumference of diamond 20 and for each of the stored images at different rotational positions. Thus, if there are n pixels in the circumference of diamond 20, and 45 images at different rotational positions, the light intensity level is averaged over 45*n pixels in total. This results in an average light intensity level for diamond 20 over all images at different rotational positions, which provides an objective measure of the brilliance of diamond 20.

To calculate a measure of the scintillation of diamond 20, the difference in light intensity levels (ie brightness) between a pixel from a first image (captured at a first rotational position) and its corresponding pixel (at the same coordinate position) from a second image (captured at a second rotational position, one rotational step after the first rotational position) is determined. This is repeated for all pixels within the circumference of diamond 20 in the first and second images, and for all pairs of first and second images captured at rotational positions which are one rotational step apart. Thus, if there are n pixels in the circumference of diamond 20, and 45 images at different rotational positions, 44*n differences are calculated. The number of times the absolute difference in light intensity levels is greater than a predetermined threshold is counted for all pixels in the circumference and for all pairs of images which are one rotational step apart. The ratio of this number over the total number of pixel pairs, 44*n, gives an objective measure of the scintillation of diamond 20.

To calculate a measure of the symmetry of diamond 20, for the composite image, composed of the stored images at each of the different rotational positions, pixels within the circumference of diamond 20 are divided into 8 approximately equal radial sectors about the centre of diamond 20. The number of sectors is chosen to correspond to the 8-fold symmetry of the SRB cut pattern. Thus, if there are n pixels within the circumference of diamond 20 in an image, each sector has approximately n/8 pixels. Then, the difference in light intensity levels (ie brightness) between each pixel in each of the 8 sectors of an image and its corresponding pixels (ie the corresponding pixels as rotated by $i \times 45°$, where i=1 to 7) in the seven other sectors of the same image is determined. Thus $(7+6+5+4+3+2+1)*n/8=7*n/2$ differences are calculated. The average of the absolute values of these differences is then calculated to give an objective measure of the symmetry of diamond 20.

In alternative embodiments of the present invention a measure of the fire of diamond 20 may be calculated by using an algorithm similar to that for determining scintillation. However, instead of measuring the difference in light intensity levels, the difference in the relative proportions of colour components (ie red, green, and blue (RGB)) between a pixel from a first image (captured at a first rotational position) and its corresponding pixel (at the same coordinate position) from a second image (captured at a second rotational position, one rotational step after the first rotational position) are determined. This is repeated for all pixels within the circumference of diamond 20 in the first and second images, and for all pairs of first and second images captured at rotational positions which are one rotational step apart. For each pixel pair, the number of times the absolute difference in the relative proportions of any of the three colour components is greater than a predetermined threshold is counted for all pixels in the circumference and for all pairs of images which are one rotational step apart. The ratio of this number over the total number of pixel pairs gives an objective measure of the fire of diamond 20.

It will be appreciated that, with different shapes and/or symmetries of particular gemstone cut patterns, such as square, oval, pear, heart-shaped or irregular shapes, the algorithms used to determine the periphery of the gemstone and the various measurements of optical properties, as described above, may be varied to take into account the shape and symmetry of the particular gemstone cut pattern.

It will be appreciated that, with different shapes and/or symmetries of particular gemstone cut patterns, such as square, oval, pear, heart-shaped or irregular shapes, the configuration of relatively reflective regions 40 and relatively unreflective regions of concave surface 26, may be varied to take into account the shape and symmetry of the particular gemstone cut pattern. It will also be appreciated that the configuration of relatively reflective regions 40 and relatively unreflective regions of concave surface 26 may be varied to take into account a particular property being determined. For instance, when determining a measure of the fire of a gemstone, it is desirable to for relatively reflective regions 40 to be thin radial lines arranged around the axis 22, such that the light pattern reflected comprises relatively narrow peaks and relatively wide troughs. Thus, spectrally coloured light will be generally less overpowered by white light and more visible.

It will be appreciated that in alternative embodiments, concave surface 26 may be held stationary within the apparatus and the platform is rotated instead. In this arrangement, the images captured of diamond 20 rotate and extra processing is required to take that into account when analysing those images. When comparing a first image at a first rotational position with a second image at a second different rotational position (and with subsequent third, fourth . . . images) processing must be performed so that pixels of the first and second (and subsequent) images correspond to the same region or regions of diamond 20. To achieve this, the second (and subsequent) image may be digitally rotated back about the point corresponding to the centre of rotation of the platform to correct for the rotation of diamond 20 in the images. Alternatively, when comparing selected pixels of a first and second (or subsequent) image, to obtain a measure of scintillation for example, the pixels of the second (or subsequent) image may be selected so as to correspond to a portion of the image rotated back about the point corresponding to the centre of rotation of the platform to correct for the rotation of diamond 20. However, due to limitations on the resolution of the captured images, accuracy of comparison is reduced in both cases and this arrangement is less preferable than the former arrangement in which the platform is stationary and concave surface 26 rotated.

It will be appreciated that in further alternative embodiments, concave surface 26 may be held stationary within the apparatus, and instead the camera 30 and the platform both rotated by a single or separate stepper motors in a coordinated fashion. This arrangement eliminates the need for extra processing to correct for the rotation of the images of diamond 20, but involves additional mechanical complexity and increased cost of manufacture.

While the above embodiment has described an apparatus arranged to i) support a gemstone having an axis of symmetry such that the axis of symmetry is parallel to the axis 22, ii) rotate the light pattern relative to the platform about the axis 22, and iii) capture images of the gemstone along the axis 22, it is important to realise that the present invention is not limited to this particular arrangement of the three axes, although this arrangement is generally preferred. In particular, the axis of relative rotation between the light pattern and the platform need not be co-linear or even parallel to the axis 22 (ie from the axis parallel to an axis of symmetry of a gemstone when supported in the apparatus) and/or the axis along which the images are captured need not be co-linear or even parallel to the axis 22. Furthermore, the axis of relative rotation between the light pattern and the platform and the axis along which the images are captured need not be co-linear or even parallel between themselves.

What is important is that a gemstone having an axis of symmetry may be supported in the apparatus such that the axis of symmetry, the axis of relative rotation between the light pattern and the means of support, and the axis along which the images are captured are coordinated such that i) the apparatus is able to take advantage of the shape and/or symmetry of the cut pattern of the particular gemstone when rotating the light pattern relative to the gemstone, and ii) the apparatus is able to capture images of the gemstone, such as images of the crown of a SRB cut diamond, from which features resulting from the shape and/or symmetry of the gemstone may be observed. For instance, the axis of relative rotation between the light pattern and the means of support may be at an angle of incidence to the axis of symmetry of up to about 30° without serious degradation to the performance of the apparatus. Similarly, the axis along which the images are captured may at an angle of incidence to the axis of symmetry of up to about 45° without serious degradation to the performance of the apparatus.

What is claimed is:

1. A method of determining a property of a gemstone using image data corresponding to one or more electronic images of the gemstone, the method comprising:

selecting a first region of the gemstone;

selecting a second region of the gemstone, the second region being selected based at least in part on the second region being related to the first region in accordance with a symmetrical property of a standardized gemstone cut; and comparing the intensity of light at a first image portion with the intensity of light at a second image portion, each image portion comprising one or more pixels, wherein said first image portion and said second image portion correspond to the first region and the second region of the gemstone, respectively.

2. The method of claim 1, wherein the first and second image portions are portions of first and second images of the gemstone, respectively.

3. The method of claim 2, wherein the first and second image portions are captured prior to selection of the first and second regions.

4. A computer-readable medium encoded with a computer program, which, when executed, causes a computer to perform a method of determining a property of a gemstone, using image data corresponding to one or more electronic images of the gemstone, the method comprising:

selecting a first region of the gemstone for imaging;

selecting a second region of the gemstone for imaging, the second region being selected based at least in part on the second region being related to the first region in accordance with a symmetrical property of a standardized gemstone cut; and comparing the intensity of light at a first image portion with the intensity of light at a second image portion, each image portion comprising one or more pixels, wherein said first image portion and said second image portion correspond to a first and a second region of the gemstone, respectively.

5. A method of determining a property of a gemstone using image data corresponding to one or more electronic images of the gemstone, the method comprising:

selecting a first image portion comprising one or more pixels corresponding to a first region of the gemstone;

selecting a second image portion comprising one or more pixels corresponding to a second region of the gemstone, the second image portion being selected based at least in part on the second region being related to the first region in accordance with a symmetrical property of a standardized gemstone cut; and comparing the intensity of light at the first image portion with the intensity of light at the second image portion.

6. The method of claim 5, wherein the first and second image portions are portions of first and second images of the gemstone, respectively.

7. The method of claim 6, wherein the first and second image portions are captured prior to selection of the first and second regions.

8. A computer-readable medium encoded with a computer program, which, when executed, causes a computer to perform a method of determining a property of a gemstone, using image data corresponding to one or more electronic images of the gemstone, the method comprising:

selecting a first image portion comprising one or more pixels corresponding to a first region of the gemstone;

selecting a second image portion comprising one or more pixels corresponding to a second region of the gemstone, the second image portion being selected based at least in part on the second region being related to the first region in accordance with a symmetrical property of a standardized gemstone cut; and comparing the intensity of light at a first image portion with the intensity of light at a second image portion.

* * * * *